US00PP11416P

United States Patent [19]

Walden

[11] Patent Number: Plant 11,416

[45] Date of Patent: Jun. 13, 2000

[54] MINIATURE ROSE PLANT NAMED 'JACMOBLI'

[75] Inventor: John K. Walden, Thousand Oaks, Calif.

[73] Assignee: Bear Creek Gardens, Inc., Medford, Oreg.

[21] Appl. No.: 09/123,183

[22] Filed: Jul. 27, 1998

[51] Int. Cl.[7] ..... A01H 5/00

[52] U.S. Cl. ..... Plt./121

[58] Field of Search ..... Plt./116, 121, 123, Plt./128

[56] References Cited

U.S. PATENT DOCUMENTS

P.P. 4,031 3/1977 Moore ..... Plt./121

OTHER PUBLICATIONS

UPOV–ROM, 1999/02, Plant Variety Database, GTI Jouve Retrieval Software, citation for 'Jacmobli'.

*Primary Examiner*—Howard J. Locker

*Attorney, Agent, or Firm*—Klarquist Sparkman Campbell Leigh & Whinston, LLP

[57] ABSTRACT

A miniature rose plant having pink flowers; vigorous, upright, compact habit; flowers that are long-lasting on the plant; dark green foliage; and disease resistance to powdery mildew.

1 Drawing Sheet

The present invention relates to a new and distinct variety of rose plant of the miniature class which was originated by me by crossing an unnamed seedling (whose parents are unnamed seedling×'Watercolor', U.S. Plant Pat. No. 4,031), with the variety 'RUImired', U.S. Plant Pat. No. 5,770.

The primary objective of this breeding was to produce a new pot rose variety having pink flower color, flowers borne in small clusters, flowers between 1½" to 3" when fully open, long lasting individual flowers, and an upright, compact plant habit suitable for greenhouse propagation from softwood cuttings. The objective was substantially achieved, along with other desirable improvements, as evidenced by the following unique combination of characteristics that are outstanding in the new variety and that distinguish it from its parents, as well as from all other varieties of which I am aware:

1. Pink, 2" flowers borne in clusters of three to five flowers;
2. Vigorous, upright, compact habit;
3. Flowers that are long lasting on the plant;
4. Dark green, abundant foliage; and
5. Disease resistance to powdery mildew.

The seed hip is pear shaped, approximately ⅞" long by ⅝" wide, and when young is near Yellow-Green Group 144A. As the hip matures, it becomes Orange Group 24A in color. The flower has a light, sweet fragrance.

Asexual reproduction of this new variety by cuttings, as performed at Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—Unnamed seedling (unnamed seedling× 'Watercolor', U.S. Plant Pat. No. 4,031).

*Pollen Parent*.—'RUImired' (U.S. Plant Pat. No. 5,770).

Classification:

*Botanical*.—Rosa hybrida.

*Commercial*.—Miniature rose.

FLOWER

Observations made Jun. 29, 1998, from specimens grown in a greenhouse environment at Somis, Calif.

Blooming habit: Continuous.

Bud:

*Size*.—About ⅝ to ¾ inch long when the petals start to unfurl.

*Form*.—The bud form is long, pointed ovoid.

*Color*.—When sepals first divide, bud color is Red-Purple Group 58B. When half blown, the upper sides of the petals are near Red-Purple Group 61D with a small Yellow Group 10C. crescent at the point of petal attachment, and the lower sides of the petals are Red-Purple Group 58C.

*Sepals*.—Color: Near Green Group 143A, with a prominent Yellow-Green Group 144C deltoid spot at sepal base, and a line of the same color that longitudinally bisects the sepal. Surface texture: Smooth. There are three lightly to normally appendaged sepals. There are two unappendaged sepals with hairy edges.

*Receptacles*.—Color: Yellow-Green Group 144B. Shape: Funnel. Size: Small, slender (about ¼"×3/16"). Surface: Smooth.

*Peduncle*.—Length: Long (1½"). Surface: Smooth. Color: Yellow-Green Group 144B. Strength: Erect and slightly bending.

Bloom:

*Size*.—Medium. Average open size is two inches.

*Borne*.—Several together in pyramidal clusters of three to five blooms.

*Stems*.—Short to normal. Average length is about 7½ inches.

*Form*.—When first open: Cupped. Permanence: Retains its form to the end. Outer petal edges curl slightly and are quilled moderately.

*Petalage*.—Number of petals under normal conditions: 40–45.

*Color*.—The upper sides of the petals are Red-Purple Group 61D on the outer two-thirds, lightening to Red-Purple Group 62C near the bottom third of petal. The reverse sides of the petals are Red-Purple Group 61D on the their outer two-thirds, lightening to Red-Purple Group 62C near the bottom third of petal. The base of each petal has a Yellow Group 5D spot at its point of attachment, blending into the Red-Purple Group 62C coloration. The major color on the upper sides is Red-Purple Group 61D.

*Variegations*.—None.

*Discoloration*.—At the end of the first day: Red-Purple Group 61D. At the end of the third day: Between Red-Purple Group 62A and 61D.

*Fragrance*.—Moderate.

Petals:

*Texture*.—Leathery.

*Shape*.—Pointed, deltoid.

*Form*.—Tips slightly recurved.

*Arrangement*.—Imbricated; shingle like. Petaloids in the center are few, small.

*Persistence*.—Petals drop off cleanly before drying.

*Lastingness*.—On the plant: Long (12 days). As a cut flower: Not tested.

Reproductive parts:

*Anthers*.—Size: Small. Quantity: Many. Color: Yellow-Orange Group 22A. Arrangement: Regular around styles.

*Filaments*.—Color: Yellow Group 12D.

*Pollen*.—Color: Gold-yellow.

*Styles*.—Color: Red Group 46A.

*Stigmas*.—Color: White.

Plant:

*Form*.—Bush, miniature.

*Growth*.—Vigorous, dwarf, upright, compact.

*Mature plant*.—Height: 18–20 inches. Width: 20 inches.

Foliage: Number of leaflets on normal mid-stem leaves: Five, occasionally seven.

*Size*.—Small, (about 3⅝ inches long×2 inches wide).

*Quantity*.—Normal.

*Color*.—New foliage: Upper surface: Yellow-Green Group 146A. Lower Surface: Greyed-Purple Group 185B. Old foliage: Upper surface: Near Green Group 139A. Lower surface: Green Group 147B.

*Shape*.—Pointed oval.

*Texture*.—Upper side: Leathery; glossy.

*Edge*.—Serrated.

*Serration*.—Single, small.

*Petiole rachis*.—Color: Green.

*Petiole underside*.—With prickles.

*Stipules*.—Short (about ⅜ to 7/16" long), serrated.

*Disease resistance*.—Resistant to mildew under normal growing conditions at Somis, Calif.

Wood:

*New wood*.—Color: Yellow-Green Group 144B with a hint of reddish coloration. Bark: Smooth.

*Old wood*.—Color: Yellow-Green Group 146B. Bark: Smooth.

Prickles:

*Quantity*.—On main canes from base: Ordinary. On laterals from main canes: Ordinary.

*Form*.—Long, straight, slightly hooked upward.

*Color when young*.—Green at tip and reddish at base.

*Color when mature*.—Brown.

Small pickles:

*Quantity*.—On main stalks: None. On laterals: None.

I claim:

1. A novel rose plant of the miniature class as herein shown and described, characterized particularly as to novelty by its pink flowers; vigorous, upright, compact habit; flowers that are long-lasting on the plant; dark green foliage; and disease resistance to powdery mildew.

* * * * *

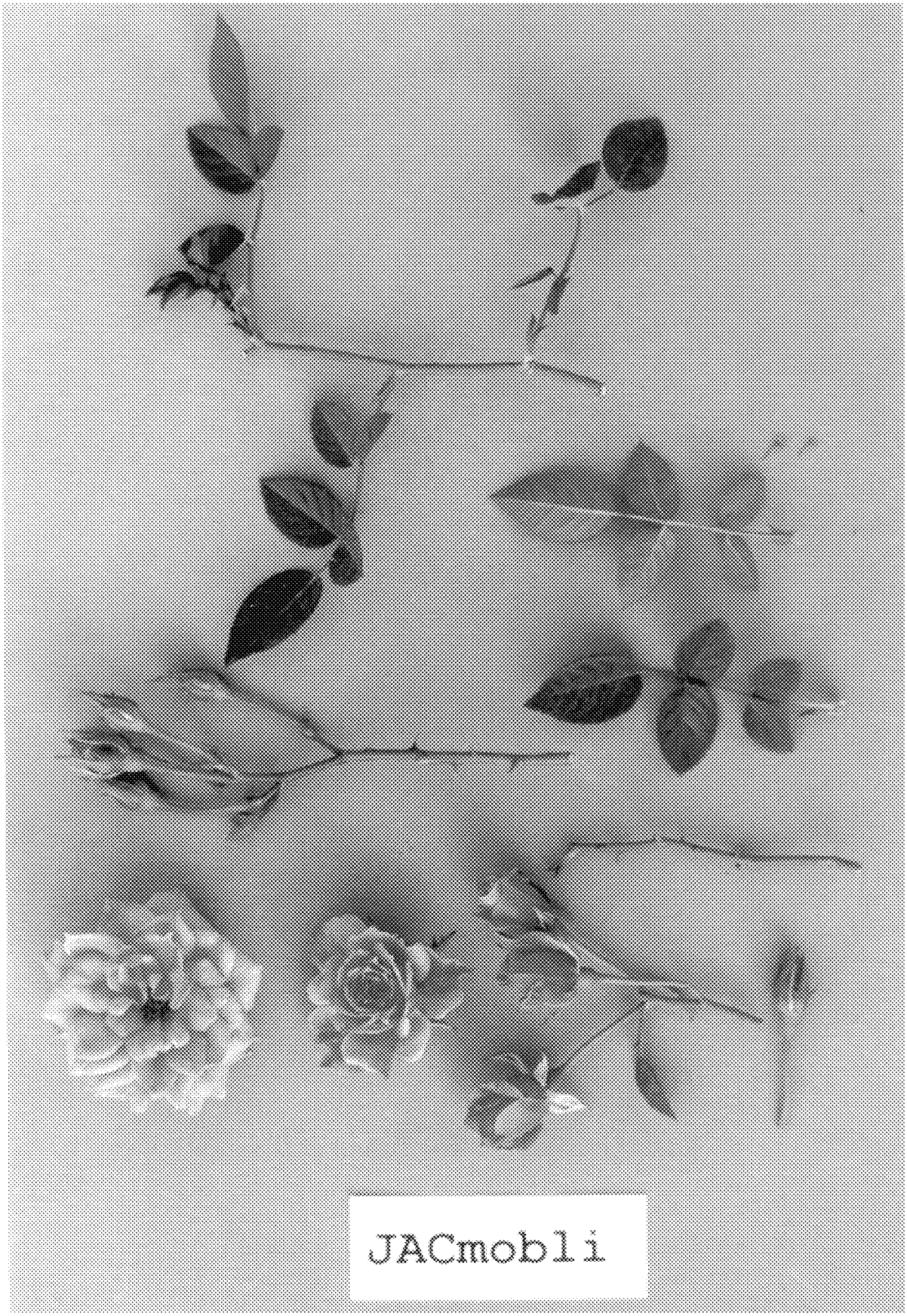
JACmobli